United States Patent
Chamney et al.

(10) Patent No.: US 10,449,285 B2
(45) Date of Patent: Oct. 22, 2019

(54) METHOD FOR CONTROLLING A BLOOD TREATMENT APPARATUS AND APPARATUSES

(71) Applicant: FRESENIUS MEDICAL CARE DEUTSCHLAND GMBH, Bad Homburg (DE)

(72) Inventors: Paul Chamney, near Tring (GB); Pascal Kopperschmidt, Dittelbrunn (DE); Wolfgang Wehmeyer, Tübingen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 662 days.

(21) Appl. No.: 14/905,431

(22) PCT Filed: Jul. 15, 2014

(86) PCT No.: PCT/EP2014/065119
§ 371 (c)(1),
(2) Date: Jan. 15, 2016

(87) PCT Pub. No.: WO2015/007721
PCT Pub. Date: Jan. 22, 2015

(65) Prior Publication Data
US 2016/0158430 A1 Jun. 9, 2016

(30) Foreign Application Priority Data

Jul. 15, 2013 (DE) .......... 10 2013 011 715

(51) Int. Cl.
*A61M 1/36* (2006.01)
*A61M 1/16* (2006.01)
(Continued)

(52) U.S. Cl.
CPC ........ *A61M 1/3644* (2014.02); *A61M 1/1601* (2014.02); *A61M 1/1603* (2014.02);
(Continued)

(58) Field of Classification Search
CPC .......... A61M 1/34; A61M 1/341; A61M 1/36; A61M 1/3609; A61M 1/3643;
(Continued)

(56) References Cited

U.S. PATENT DOCUMENTS

| 4,670,152 A | 6/1987 | Leonard |
| 5,863,421 A * | 1/1999 | Peter, Jr. ................... A61L 2/04 210/134 |

(Continued)

FOREIGN PATENT DOCUMENTS

| CN | 102438676 | 5/2012 |
| DE | 196 55 226 B4 | 1/2009 |

(Continued)

OTHER PUBLICATIONS

International Search Report from PCT/EP2014/065119, dated Mar. 3, 2015.
(Continued)

*Primary Examiner* — John Kim
(74) *Attorney, Agent, or Firm* — Fish & Richardson P.C.

(57) ABSTRACT

The present invention relates to a method for controlling a blood treatment apparatus, with the conveying of blood using a blood pump, with the patient venous tubing clamp closed, until a predetermined volume of fluid has passed out of the blood tubing set through the membrane and into the dialysis fluid chamber. It also relates to a control and regulating apparatus and a treatment apparatus. It further relates to a computer program, a computer program product and a digital storage medium.

19 Claims, 6 Drawing Sheets

(51) Int. Cl.
*A61M 1/34* (2006.01)
*A61M 39/28* (2006.01)

(52) U.S. Cl.
CPC .............. *A61M 1/168* (2013.01); *A61M 1/34* (2013.01); *A61M 1/341* (2014.02); *A61M 1/36* (2013.01); *A61M 1/365* (2014.02); *A61M 1/3609* (2014.02); *A61M 1/3626* (2013.01); *A61M 1/3643* (2013.01); *A61M 1/3646* (2014.02); *A61M 1/3647* (2014.02); *A61M 1/3649* (2014.02); *A61M 1/3653* (2013.01); *A61M 1/3659* (2014.02); *A61M 1/3661* (2014.02); *A61M 39/28* (2013.01); *A61M 2202/0413* (2013.01); *A61M 2205/3331* (2013.01); *A61M 2205/50* (2013.01)

(58) Field of Classification Search
CPC .. A61M 1/3644; A61M 1/365; A61M 1/3661; A61M 1/1601; A61M 1/1603; A61M 1/168; A61M 1/3626; A61M 1/3646; A61M 1/3653; A61M 1/3659; A61M 2202/0413; A61M 39/28; A61M 2205/3331; A61M 2205/50
See application file for complete search history.

(56) References Cited

U.S. PATENT DOCUMENTS

| | | | |
|---|---|---|---|
| 5,932,103 A * | 8/1999 | Kenley | A61L 2/04 210/108 |
| 2008/0215247 A1* | 9/2008 | Tonelli | A61M 1/16 702/19 |
| 2011/0213289 A1* | 9/2011 | Toyoda | A61M 1/3643 604/6.09 |

FOREIGN PATENT DOCUMENTS

| | | |
|---|---|---|
| DE | 10 2009 018664 A1 | 10/2010 |
| JP | 2532261 | 6/1996 |
| JP | 2000-325470 | 11/2000 |
| JP | 2006-271514 | 10/2006 |
| JP | 2010-253129 | 11/2010 |

OTHER PUBLICATIONS

Horl et al., "Dialyseverfahren in Klinik un Praxis," Technik und Klinik, 6th Edition, Thieme Verlag, Stuttgard 2004 [ISBN3-13-497706-0, pp. 183-184]. (with partial translation).

* cited by examiner

METHOD FOR CONTROLLING A BLOOD TREATMENT APPARATUS AND APPARATUSES

CROSS REFERENCE TO RELATED APPLICATIONS

The present application is the national stage entry of International patent application Ser. No. PCT/EP2014/065119, filed on Jul. 15, 2014, the disclosure of which is expressly incorporated herein in its entirety by reference thereto, and claims priority to Application No. DE 10 2013 011 715.1, filed in the Federal Republic of Germany on Jul. 15, 2013.

FIELD OF INVENTION

The present invention relates to a method for controlling and/or regulating a blood treatment apparatus, in particular for preparing an extra-corporeal blood tubing set. It also relates to a method for admitting a fluid. It further relates to a control or regulating apparatus, a blood treatment apparatus, a computer program, a computer program product and a digital storage medium.

BACKGROUND

Methods for controlling a blood treatment apparatus are known from practice—amongst other things—for priming or rinsing, for example, of an extra-corporeal blood tubing set to prepare it for its use in a blood treatment.

SUMMARY

One object of the present invention is to propose further methods for controlling or regulating a blood treatment apparatus. Further, a control (open loop) or regulating (closed loop) apparatus and a blood treatment are proposed.

In addition, a computer program, a computer program product and a digital storage medium are proposed.

The object of the present invention can be solved with a method of the present invention. Further, it can be solved with a control or regulating apparatus, a blood treatment apparatus, a computer program, a computer program product and a digital storage medium.

Thus, according to the present invention, a—preferably automatic—method for controlling and/or regulating a blood treatment apparatus which features or comprises (feature and comprise are used exchangeably herein) a pressure or vacuum source for conveying blood within an extra-corporeal blood circuit—for example a blood pump for pumping or an ultra-filtration pump for suctioning—is proposed. All these alternatives, which can also be assembled in combination, are also shortened to "pumps" or "blood pumps" below, which are not restrictive, but are to be understood instead in the sense in which they have already been described here. The blood tubing set can feature one or more of the following elements or can be connected therewith. For instance, the blood tubing set can feature an arterial section which features an arterial needle—or is connected therewith—and an arterial patient tubing clamp. The blood tubing set can further feature a venous section which features a venous needle—or is connected therewith—and a patient tubing clamp. At least one blood filter can be arranged between the arterial and the venous sections. This features a membrane. The membrane divides or separates a blood chamber and a dialysis fluid chamber.

The method according to the present invention encompasses the conveying of a fluid (this can be blood, a fluid mixture, a mixture such as blood foam, or another fluid with portions of air or gas, saline solution, priming solution or the like, which is why the term "fluid" as it is used below is to be understood as it is exemplarily defined here), using a blood pump with the venous patient tubing clamp closed. This can involve the conveying of fluid for the first time or at the start of the blood treatment session, or the conveying of a fluid before blood has first flowed through the venous section or through the venous needle in the direction of the patient.

The arterial section of the blood tubing set lies upstream of the blood filter. The venous section of the blood tubing set lies downstream from the blood filter. With respect to the above sentence, the terms "upstream" or "in an upstream direction" signify herein that in usual usage of the blood treatment apparatus, the extracorporeal blood flows initially through the arterial section and only after that, through the blood filter.

The control or regulating apparatus according to the present invention is arranged, configured, intended and/or programmed to execute a method according to the present invention, or to prompt its execution, in co-operation with a blood treatment apparatus equipped with the devices required for this purpose.

The blood treatment apparatus according to the present invention features a control or regulating apparatus or is connected with this.

The computer program according to the present invention can be loaded directly onto the internal memory of a digital computer and includes sections of software code with which the steps of the method according to the present invention can be executed, or are achievable, when the computer program runs on a computer.

The digital storage medium according to the present invention features electrically readable control signals which can interact with a programmable computer system or computer, such that the steps of a method according to the present invention can be prompted.

A particularly digital, particularly non-volatile, storage medium according to the present invention (also termed here as a carrier), particularly in the form of a diskette, RAM, ROM, CD, hard disk, DVD, USB stick, flashcard, SD card or EPROM, particularly with electrically or optically readable control signals, can interact with a computer or computer system in such a way that the mechanical steps of the method according to the present invention, as described herein, can be prompted)

Thereby all, some, or a few of the mechanically implemented steps of the method according to the present invention can be prompted.

A computer program product according to the present invention features a volatile, non-permanent, or a machine readable carrier or program code, saved on a storage medium, for prompting the steps of the method according to the present invention when the computer program product runs on a computer. A computer program product can, according to the present invention, be understood as, for example a computer program saved on a carrier, an embedded system as a comprehensive system with a computer program (e.g., an electronic appliance with a computer program), a network of computer implemented computer programs (e.g. a client-server system, Cloud computing system, etc.), or a computer on which a computer program is loaded, run, saved, implemented or developed.

A machine readable carrier designates in certain embodiments according to the present invention according to the present invention a carrier which contains software and/or hardware interpretable data. The carrier can be a diskette, a CD, DVD, a USB stick, a flashcard, an SD card and the like.

A computer program according to the present invention includes a program code for prompting the mechanical steps of a method according to the present invention when the computer program runs on a computer. According to the present invention a computer program can be understood as, for example, a physical software product which is ready for use and features a program.

It is also true of the computer program product and the computer program according to the present invention that all, a few or some of the mechanically implemented steps of the method according to the present invention can be executed.

In all of the above and following explanations, the use of the expressions "can be", e.g., "can haves" etc., are to be understood as synonyms for "is preferable" "preferably has", etc., and are intended to illustrate an embodiment according to the present invention.

Embodiments according to the present invention can feature one or several of the features/characteristics referred to below.

In some embodiments according to the present invention, during the conveying of fluid, the fluid present in the venous section is completely or partially not blood, for example a priming solution. A priming solution can contain or consist of a saline solution, a dialysis fluid preparation, a mixture of known fluids or another fluid.

In some embodiments according to the present invention a venous patient tubing clamp which is completely or partially closed, is also to be understood as a patient tubing clamp, which causes a noticeable restriction or slowing down of the flow through the venous section in such a way that, by virtue of the pumping action of the blood pump, fluid passes through the membrane of the blood filter positioned upstream of the patient tubing clamp. In other embodiments according to the present invention a closed venous patient tubing clamp permits no flow of fluid across the membrane.

In some embodiments according to the present invention, the venous patient tubing clamp is any device for interrupting or restricting or slowing down the flow in the venous section of the blood tubing set downstream of the blood filter.

In some embodiments according to the present invention, the arterial patient tubing clamp is each device for interrupting or restricting or slowing down the flow in the arterial section of the blood tubing set upstream of the blood filter.

In certain embodiments according to the present invention, fluid is pumped or suctioned or conveyed, for example by a dialysate and/or ultra-filtration pump, until—preferably at least or at most—a predetermined volume of fluid has passed through the membrane out of the blood tubing set, in particular out of its arterial section, and into the dialysis fluid chamber.

The volume of fluid which passes through the membrane into the dialysis fluid chamber as a predetermined volume, can be termed ultra-filtrate.

In some embodiments according to the present invention, the predetermined volume which passes across or through the membrane can result from a predetermined period of time during which the blood pump runs at a predetermined delivery rate.

Below the term "tubing clamp" is used as an alternative for the term "patient tubing clamp".

In certain embodiments according to the present invention, the fluid is conveyed, as ultra-filtrate by the blood pump, with the venous tubing clamp closed, out of the blood tubing set, through the membrane and into the dialysis fluid chamber until, at least, a sensor signal transmits, indicates or codes for the arrival of blood at a predetermined location.

A "predetermined location" can be at or in the blood filter (in the blood chamber or in the dialysis fluid chamber). The "predetermined location" can, however, also be upstream or downstream (downstream only if the patient tubing clamp is not completely closed) of the blood chamber, on the blood side or on the dialysate side. The dialysate side follows on upstream and downstream from the dialysis fluid chamber In some embodiments according to the present invention, the sensor signal is a pressure signal.

In certain embodiments according to the present invention, the period between the start of the conveying of fluid and the point at which blood is first detected by a sensor signal is termed the first phase or Phase 1.

In certain embodiments according to the present invention, the delivery of fluid is reduced or stopped after a predetermined volume of fluid passes into the dialysis fluid chamber, or at least when a sensor signal has detected or transmitted the arrival of blood at a predetermined location. This phase in which the conveying of fluid is reduced or stopped is termed below as the second phase or phase 2.

In some embodiments according to the present invention, in the second phase the conveyed fluid mixes increasingly with the blood conveyed subsequently. With the advancing of the delivery period, the portion of blood can increase in relation to the portion of fluid. In the second phase, the portion of fluid which passes through the membrane out of the blood tubing set into the dialysis fluid chamber as ultra-filtrate, can be reduced. In some embodiments according to the present invention, the venous tubing clamp is completely or partially opened in order to achieve this constant or near constant delivery or conveying rate by the blood pump which, in the second phase, conveys the mixture of fluids, in particular the mixture of priming fluid and blood. In this way, at least one part of the conveyed volume flows through the venous section. Alternatively or complementarily, the pump's volume output can be appropriately lowered.

In certain embodiments according to the present invention, the reduction in fluid passing as ultra-filtrate out of the blood tubing set through the membrane into the dialysis fluid chamber is achieved in a linear or non-linear way with advancing time periods, e.g., progressive or degressive.

In some embodiments according to the present invention the pressure signal, which as a sensor signal transmits the arrival of blood at a predetermined location, does so on the basis of pressure pulses emitted or transmitted from the blood pump. These pressure pulses are transmitted through, by, or along the conveyed volume (fluid and/or blood) and can run transversally through the pores of the blood filter membrane.

The pressure pulses can, for example, be detected or analysed on the dialysis fluid chamber side or in the supply or discharge lines of the dialysis fluid chamber—hence, on the hydraulic side—using at least one of the pressure sensors provided for this purpose.

In some embodiments according to the present invention, a device which is arranged, configured, prepared and/or programmed for evaluating, identifying or comparing such pressure signals is provided.

In certain embodiments according to the present invention the pressure sensors for detecting and analysing the pressure pulses are, according to the present invention, pressure sensors used in or with the blood treatment apparatus in order to measure or determine arterial or venous pulses, or intended for this purpose.

In certain embodiments according to the present invention, the pressure pulse amplitudes detected by the pressure sensor are analysed. These pressure amplitudes which are produced or generated and sent from the blood pump at certain time intervals, for example based on the engagement of the rollers of a roller pump, can change over the progression of time. In the following, the pressure amplitudes detected, for example, in the dialysis fluid chamber (or their supply and discharge lines) are termed as output amplitudes, and pressure amplitudes detected by the pressure sensor in or at the blood tubing set, for example—preferably between the blood pump and blood filter—are termed input amplitudes. In the first phase (Phase 1) a fixed relationship between output and input amplitude can occur with regard to the blood chamber. If the damping of the pressure pulses in the fluid increases, i.e., if the output amplitude decreases in relation to the input amplitude, this can be an indicator for the start of a mixture of fluid with blood that follows. The start of the mixture of fluid with blood can mark the end of phase 1 or the start of a following phase 2.

In some embodiments according to the present invention, the decrease or reduction in fluid passing through the membrane into the dialysis fluid chamber (this volume flow is also termed ultra-filtrate flow below) is determined or identified by the output amplitudes of the corresponding pressure sensors (see above).

If the input amplitudes (see above) are not known then in certain embodiments according to the present invention, the output amplitudes can, for example, be used alone as the starting point and/or the extent for the—particularly required—reduction of the ultra-filtrate flow, particularly in the manner explained above.

In some embodiments according to the present invention the output amplitudes are detected—preferably alone—at the pressure sensor for determining the flow of the ultra-filtrate, for example as modulation range $A_{out}$ of the pressure fluctuations within the fluid, particularly of the output amplitudes.

The ultra-filtrate flow can be determined using the following equation or formula:

$$Q_{UF}(t) \propto \alpha \cdot Q_B \cdot \frac{A_{out}(t)}{A_{out}(t=0)} \quad (1)$$

with:

$Q_{UF}$ (t): chronological sequence of the ultra-filtrate flow through the membrane;

$Q_B$: blood flow;

α: coefficient which indicates which share of the blood flow $Q_B$ should be filtered across the membrane in Phase 2;

$A_{out}$ (t): modulation range of the pressure pulse fluctuations at time point t; and $A_{out}$ (t=0): modulation range of the pressure pulse fluctuations at time point t=0; the time point t=0 can be the start of the consideration or analysis and/or the method according to the present invention.

The extent by which the ultrafiltration should be reduced can be identified with the formula (1). In certain embodiments according to the present invention this is dependent on increasing portions of blood to the conveyed fluid.

In some embodiments according to the present invention, $Q_{UF}$ (t) is set at the ultra-filtration pump.

$Q_B$ is set at the blood pump in some embodiments according to the present invention.

In certain embodiments according to the present invention, the sensor signal is an optical signal.

The optical signal is detected with optical sensors known to the person skilled in the art. With the help of an optical sensor which can detect, for example, the fluid and/or the blood by a colour change—in the blood chamber or another position, for example—it is possible to identify or determine the start of the second phase. The detection of the start of the second phase can bring about a reduction or cessation of the conveying of fluid and/or blood, this being initiated by a control or regulating device according to the present invention, for example.

In some embodiments according to the present invention, the predetermined amount of volume corresponds completely, in part, substantially or by a predetermined portion with the volume of priming solution which is passed out of the arterial section, by the blood pump, through the membrane and into the dialysis fluid chamber.

According to the present invention, "priming solution" is to be understood as every fluid which is used to fill and/or wash the blood tubing set before the start of the blood treatment. Usually, this would be dialysis fluid or substitute fluid. The priming solution can be a sterile, physiologically compatible solution.

In certain embodiments according to the present invention, the predetermined volume amount corresponds with the total volumetric capacity of the blood tubing set, or a section hereof. The total volumetric capacity can correspond, for example, to the volumetric capacity of the blood tubing set lines without blood filter or with blood filter, or with the blood chamber of the blood filter only. A section of the blood tubing set can be the arterial section without blood filter, or with blood filter, or with the blood chamber of the blood filter only.

In some embodiments according to the present invention, the method encompasses an output or a dispatch of a control instruction to the blood treatment apparatus or a data receiver, wherein the control instruction is able to prompt the treatment apparatus to filter at a higher ultra-filtration rate in a first time period—or it is accordingly set to filter at a higher ultra-filtration rate—than in a second time period following the first time period.

In certain embodiments according to the present invention the method comprises outputting a control instruction to the blood treatment apparatus such or with the effect that the latter filters during a first time period, which takes place subsequently directly or indirectly after the method as described above, with a higher ultra-filtration rate than during a second time period following the first time period, wherein the venous patient tubing clamp is open during the first and the second time period.

The term "to open" or "opening" the venous and/or the arterial patient tubing clamp refers in some embodiments according to the present invention to fully or partially opening the patient tubing clamp in order to allow a partial or full flow rate or passage of fluid and/or blood through the venous patient tubing or the blood tubing section. Opening can be done manually or automatically.

In some embodiments according to the present invention, the higher ultra-filtration rate can advantageously serve to additionally filter, during the treatment time, any possibly remaining fluid volume in the blood tubing set as priming fluid during the treatment time.

The (continuous or discontinuous) ultra-filtration rate applied during the treatment time—be this the total treatment time or only a section thereof, e.g., the first time period—and in particular, the higher ultra-filtration rate identified above, can be set in such a way that it also effects the ultra-filtration of a volume intended for the treatment of the patient in addition to its effects on the ultra-filtration volume which corresponds to the fluid volume possible remaining in the blood tubing set as a priming volume.

Figure 5:
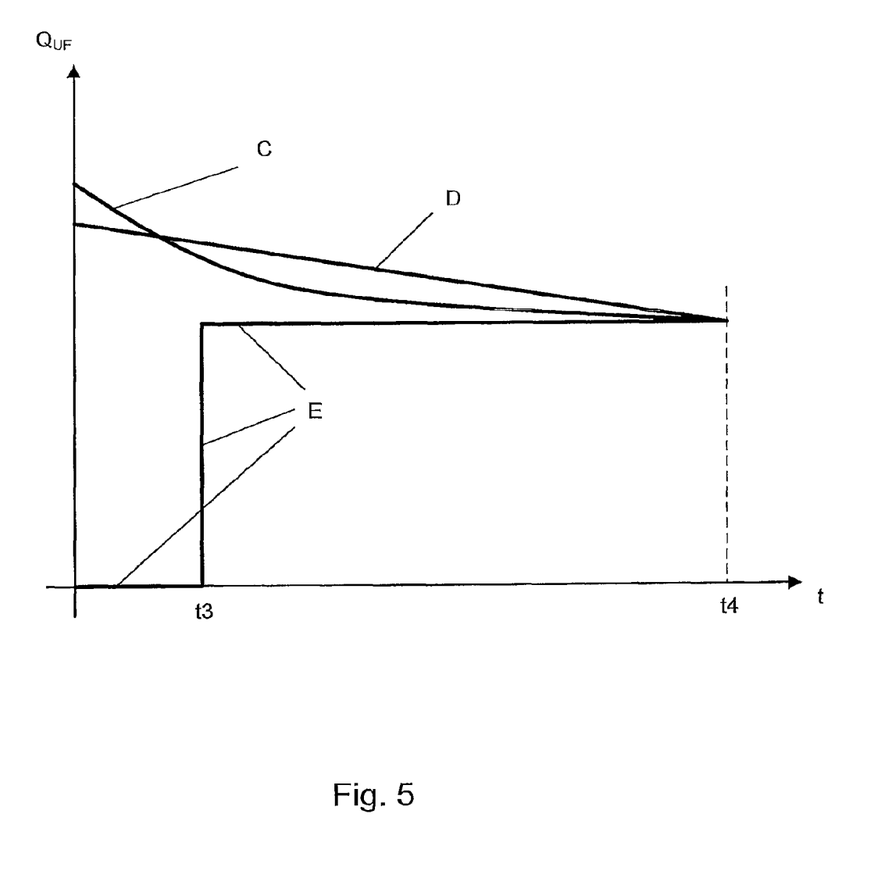
FIG. 5 shows possible chronological sequences or time courses for the flow of the ultra-filtrate across the membrane between the blood chamber and the dialysis fluid chamber.

In certain embodiments according to the present invention, the first time period lies at start of the blood treatment period and the second time period begins and ends after the end of the first time period. Possible embodiments are illustrated in FIG. 5. Among these are, for example, a linear decrease or decline of the ultra-filtration rate, a progressive decrease or decline, a degressive decrease or decline, a continuous decrease or decline, a consistent decrease or decline, or a combination of these.

In some embodiments according to the present invention the blood treatment does not include the filling of the extracorporeal blood circuit and/or those periods before the opening of the venous tubing clamp.

In certain embodiments according to the present invention, the blood treatment period includes only those periods during which the blood is cleaned, filtered or otherwise treated through contact with the blood filter. In some embodiments according to the present invention, the filling of the extracorporeal blood circuit and/or those periods which elapse before the venous tubing clamp is opened, are not included in the treatment period.

In certain embodiments according to the present invention, the ultra-filtration rate declines/decreases solely during the total duration of the first and the second time periods. In certain embodiments according to the present invention, the ultra-filtration rate declines solely during the total duration of the blood treatment.

In some embodiments according to the present invention, the control instruction causes, or codes for, the degressive decrease or decline of the ultra-filtration rate within the first time period. In certain embodiments according to the present invention the control instruction is able or adapted to effectuate a decrease or decline in the ultra-filtration rate within the first time period. In certain embodiments according to the present invention, the ultra-filtration rate is set to decrease within the first time period on receipt of the control instruction, irrespective of sensor measurement results.

In some embodiments according to the present invention, the control instruction brings about the filtering of a volume across the membrane in the first time period, which is—for example, at least or at most—higher than a volume which is filtered across the membrane in a second time period by the volume capacity blood chamber of the blood tubing set and the blood tubing set located downstream therefrom.

In some embodiments according to the present invention, the first and the second time periods are equal lengths.

In certain embodiments according to the present invention which may not feature any features characteristics or elements (wherein feature, characteristic and element are used exchangeably herein) of the above described embodiments and/or methods, but instead stands alone, the ultra-filtration rate during the treatment session is additionally raised to compensate for an additional volume delivered into the patient's vascular system (e.g. a saline solution supplied as an infusion) at the end of the treatment session. The additionally supplied volume shall or should completely or partially counteract or reduce a volume adjustment which after the end of the treatment session occurs inside of the blood vessels and the patient's two fluid compartments i.e., the extracellular matrix (abbreviated below as ECM) and the blood vessels.

In some embodiments according to the present invention, the additional supply of volume is set by determining a parameter which is a measure for the change in the portion of plasma water in the patient's blood and/or is interpreted as such a measure according to the present invention. In certain embodiments according to the present invention, possible parameters for this are the hematocrit, the haemoglobin value or other blood viscosity parameters. Devices for measuring such parameters can be provided according to the present invention. In particular, a device for measuring the hematocrit can be provided. This can be arranged, for example, to measure the hematocrit using an optical measurement, or in some other way.

In some embodiments according to the present invention, determining of the parameter takes place at at least two time points during the blood treatment session and preferably in the blood in the extracorporeal blood tubing set. Blood can be removed from the extracorporeal blood tubing set for the determining of the parameter.

In some embodiments according to the present invention, the method encompasses an issue of a control instruction to the blood treatment apparatus such that during the treatment session the treatment apparatus filters at a higher first ultra-filtration rate between two time points, which compensates for the volume supplied additionally at the end of the treatment session—as it were, before this is supplied.

In certain embodiments according to the present invention a reference value is set up or generated at the start of the treatment session, which serves as, or is determined as, a reference value for the portion of plasma water intended to be in the patient's blood by the end of the blood treatment session.

This reference value can contain the following three volumes or can consist of these: the distribution volume $V_{pat}$ (the "refilling water" originates from the distribution volume which is used in the known "refilling") comes from the distribution volume), the patient's blood volume $V_{Blut}$ (quantity of blood in the blood compartment), and the volume which will be additionally withdrawn by ultra-filtration, abbreviated as $V_{UF}$.

In certain embodiments according to the present invention, the volume of the extra cellular matrix (ECM) is simply assumed to be essentially the same as the distribution volume $V_{pat}$. $V_{pat}$ can, for example, be determined using the Watson Formula or the so called "Body Composition Monitor" (BCM) such as those distributed by the firm Fresenius Medical Care, Germany, or for example by the method disclosed in the international patent application WO 2006/002685 A1. The Watson Formula is a common, empiric, adapted quantity equation by which the water content of a body is calculated taking into account or entering defined parameters like size, weight, gender. The Watson Formula is saved at the computers of a dialysis apparatus and is basis for the Kt/V determination. By way of example Schönweiß (Schönweiß, Günther, Dialysefibel 3, Band 2, dritte, völlig neu bearbeitete und erweiterte Auflage, abakiss Verlagsgesellschaft mbH, 2006, Pages 481-482) specifies the amount of urea distribution volume V (in liters) which correspond to the body water, as follows:

Men: 2.45−[0.09×Age in years+0.11×Size in cm+0.34×weight in kg]

Women: −2.1−[0.11×Size in cm+0.25×weight in kg]

This adapted quantity equation can also be found in Hörl and Wanner (Hörl, W. H.; Wanner C., Dialyseverfahren in Klinik und Praxis, 6., völlig neu bearbeitete Auflage; Georg Thieme Verlag, 2003, Page 210)

The urea distribution volume can alternatively be measured with the help of bioimpedance measurement (BCM, "Body Composition Monitor").

Hence, the volume at the start ($V_{ges, Beginn}$) of the treatment session can be determined as reference value:

$$V_{ges,Beginn} = V_{pat} + V_{Blut} + V_{UF} \quad (2)$$

The volume at the end ($V_{ges,Ende}$) of the treatment session can be determined as:

$$V_{ges,Ende} = V_{pat} + V_{Blut} \quad (3)$$

The portion or fraction of plasma water at the start of the treatment is higher by the factor x than at a point of time after ultrafiltration:

$$x = \frac{V_{pat} + V_{Blut} + V_{UF}}{V_{pat} + V_{Blut}} \quad (4)$$

In some embodiments according to the present invention the portion of all cellular constituent parts of the blood volume ($V_{ges}$) (given in percentages; 100%=1; termed below as hematocrit (HKT)) can be used to determine the plasma water portion in the blood ($V_{plasma, ges}$), as set out below:

$$V_{Plasma,ges} = V_{ges}(1 - HKT) \quad (5)$$

In this embodiment example, the total protein contribution of the blood is not considered.

Accordingly, the relationship between the hemahematocrit at the beginning ($HKT_{Beginn}$) and end ($HKT_{Ende}$) of the treatment session consists of the following relation, provided that the ECM is in equilibrium with the blood volume (the so-called refilling process no longer takes place):

$$(1 - HKT_{Beginn})(V_{pat} + V_{Blut} + V_{UF}) = (1 - HKT_{Ende})(V_{pat} + V_{Blut}) \quad (6)$$

In some embodiments according to the present invention, the volume delivered additionally into the patient's vascular system (infusion volume) is hence to be determined that at the end of the treatment session the following applies:

$$HKT_{Ende} = 1 - (1 - HKT_{Beginn})\left(\frac{V_{pat} + V_{Blut} + V_{UF}}{V_{pat} + V_{Blut}}\right) \quad (7)$$

The volume $V_{pat}$ can be assumed to be the distribution area without blood volume and without overhydration.

In certain embodiments according to the present invention, at the start of the treatment session, the hematocrit, or a portion of plasma water in the blood is determined as a reference value. Further, at or towards the end of the treatment session, the patient is given the additional volume, for example, intravenously, or preferably over or through the extracorporeal blood circuit. The ultra-filtration is regulated or controlled in such a way that by the end of the treatment session, the hematocrit or the portion of plasma water in the blood acquires a previously specified value and/or lies within a previously specified range of values.

In some embodiments according to the present invention, the hematocrit or portion of plasma water in the blood at the end of the treatment session is higher than when measured at the start.

In some embodiments according to the present invention, the hematocrit or the portion of plasma water in the blood at the end of the treatment session is, for example, between 5% to 25%, or for example, between 5% and 15%, or preferably about, or exactly, 10% higher than it is at the beginning of the treatment session, for example.

In some embodiments according to the present invention, at the end of the treatment session, the hematocrit or the portion of plasma water in the blood is higher than at the start of the treatment session by, for example, the quotient of over-hydration (measurable with the Blood Composition Monitor, BCM, or other methods and apparatuses suitable for the person skilled in the art) and distribution volume. The distribution volume may correspond to the volume which is called $V_{pat}$ here In some embodiments according to the present invention the treatment apparatus and/or the control device are correspondingly equipped, configured and/or programmed to carry out the method according to the present invention.

As the volume supplied additionally can only be determined at the end of the treatment session, but should be removed or withdrawn by ultra-filtration during the treatment session in order to safeguard the patient's total volume balance, the volume supplied additionally can or will for example be determined, acquired or approximated iteratively during one or more treatment sessions, or determined using a table.

In certain embodiments according to the present invention, the volume supplied additionally is determined on the basis of the patient's determined absolute blood volume. The patient's absolute blood volume can be specified using either a weight estimation for the patient or an estimate based on data from a measurement using a "Body Composition Monitor" (BCM) as distributed by the company Fresenius Medical Care, Germany, or, for example, as disclosed in the international patent application WO 2006/002685 A1. The estimate using the BCM is based on extracellular matrix ECM (synonym for ECW—extracellular water) and the intracellular matrix (ICM) (synonym for ICW—Intracellular Water).

In some embodiments according to the present invention, a control instruction is a machine readable, or a machine executable, instruction or a (e.g. still to be compiled) preliminary stage hereof. This can be a signal.

In certain embodiments according to the present invention the treatment apparatus is embodied for acute dialysis, chronic dialysis, or for aquapheresis, in particular as a "SCUF device" (SCUF=slow continuous ultra-filtration).

Each of the devices and apparatuses of the apparatus according to the present invention named herein are configured, controlled and/or programmed or prepared in some other way to execute each of the steps of the method, even if this is not specifically explained here.

In some embodiments according to the present invention, no vacuum is applied or created at the outlet of the dialysis fluid chamber of the blood filter.

In some embodiments according to the present invention, the blood treatment apparatus is not designed for the treatment of blood during a heart bypass operation, in particular for enrichment of oxygen.

In some embodiments according to the present invention, at least the flood filter is designed and/or intended not to be reusable and/or is not prepared for a new usage; it is rather used for only one time. Alternatively or additionally other parts of the blood tubing system or of the extracorporeal blood circuit may in this sense be designed as and/or intended to be disposable blood cassettes by way of example.

In some embodiments according to the present invention, the method encompasses a method step of conveying fluid by means of the ultrafiltration pump exclusively towards the blood filter.

The statements and definitions relating to the apparatus according to the present invention are also relevant to the method according to the present invention, and vice versa, where this gives no rise to contradiction for the person skilled in the art.

Some or all of the embodiments according to the present invention can feature one, several or all of the advantages stated above and/or below.

The present method can provide an improvement on the known method synchronous connection, which concerns the connecting of the blood tubing to the patient. By this known method, the arterial patient needle and the venous patient needle are connected simultaneously to the patient's vascular system, for example the fistula. All of the filling volume (e.g., the priming solution), which remained from the previous filling and priming of the blood tubing, is carried to the patient's the vascular system through the venous patient needle. This takes place using the blood pump, which propels the priming solution, via the suctioning of blood, into the venous patient needle and through this into the vascular system. In this way the volume of priming solution required for filling the entire blood tubing set enters the blood system of the patient.

Thereby, the volume of the priming solution needed for filling the entire blood tubing set is reflected in the fluid balance of the treatment session which necessitates a correction of the balance by adjusting at the dialysis apparatus the (desired/intended/expected) total weight loss of the patient. However, such a correction, which is undertaken by personnel but is occasionally forgotten, cannot take into consideration complex and dynamic effects such as the water rebound. These effects result in the so-called refilling of fluid which still flows out of the extra vascular space into the blood vessels after the blood treatment has ended.

The present invention reduces the correction which needs to be carried out by personnel (as described above) and the accompanying inefficiencies which can arise from the refilling processes, which in turn can result in the need to correct the fluid balance. This takes place in the following way according to the present invention: prior to the start of blood treatment a large portion of the priming solution volume necessary for the filling of the blood tubing set is advantageously removed from the blood tubing set and does not reach the patient's blood vessels at all and thereby neither does it reach the fluid balance.

Additionally, a priming solution which does not reach the patient's vascular system will not lower his/her oncotic pressure—an inflow of fluid into the extravascular space because of lowered oncotic pressure is advantageously avoided. In this way, the subsequently started blood treatment can finish earlier or be set to be carried out at a higher ultra-filtration rate; a refilling on the basis of the fluid which has passed into the extra vascular matrix because of a low oncotic pressure is advantageously prevented. An "pre-set" or "predisposed ultra-filtration, with which this refilling can be compensated a priori, is not required. A risk of patient hypertension, associated with an pre-set or predisposed ultra-filtration, can be advantageously avoided according to the present invention.

A further advantage which can be achieved according to the present invention, is that, owing to the initially elevated setting of the ultra-filtration rate during the first time period, a portion of the priming solution volume required for filling the blood tubing set is transferred, at the start of the treatment session, out of the blood tubing across the membrane into the dialysis fluid chamber. This portion will require no adjustment or balancing later which, as shown above, can be prone to error and undesired consequences. The plasma-refilling-rate—which is a desired balance between the fluid volume entering the vessels due to refilling and the fluid volume simultaneously removed from the vessels because of ultra-filtration—can be achieved very soon after the start of the treatment, due to the issuing of the control instruction according to the present invention. The later consideration of the additional volume to be ultra-filtrated, which is necessary because of the volume of the priming solution necessary for filling the blood tubing set, can be advantageously omitted. This portion can be that portion of priming solution, which has not already been transferred out of the blood tubing set across the blood filter membrane into the dialysis fluid chamber with the venous patient tubing clamp closed.

In the known state of the art method for preparing the blood tubing set for the blood treatment session, in which is also known as the bloody connection method, a large portion of the priming solution in the blood tubing set is discarded through the venous patient tubing, which is not connected to the patient, into a provided collection container. Next, the venous patient tubing is connected manually to the venous patient needle. The blood treatment can begin. In contrast to this known method, the method according to the present invention makes it possible to render the manual connecting of the venous patient tubing—which up until the point of being connected can be contaminated, for example by contact with the container for the disposal of priming solution—unnecessary. After its removal from sterile packaging, the venous patient tubing can be immediately connected to the venous patient needle and remain there. This can contribute advantageously to improved hygiene and, along with this, increased patient safety.

Further, it is not necessary to provide a collection container, which saves on costs on these as well as on the special drain connecters required for connecting the venous patient tubing to the collection container.

Below, the present invention is exemplarily illustrated with the help of the drawings, in which identical reference symbols indicate the same or similar components. In the figures, which are in part highly simplified.

BRIEF DESCRIPTION OF THE DRAWINGS

DETAILED DESCRIPTION

Figure 1:
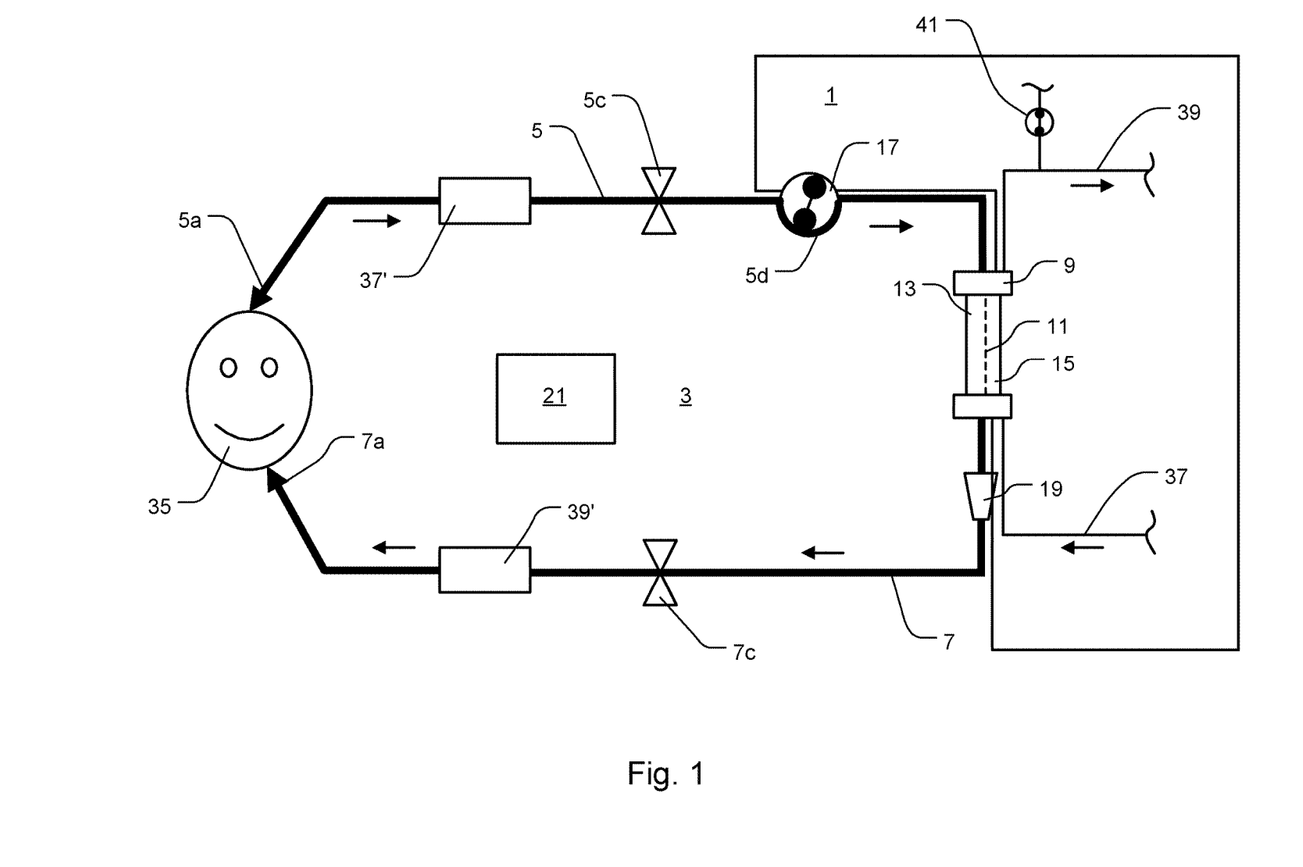
FIG. 1 shows a schematically simplified apparatus according to the present invention for executing the method according to the present invention.

FIG. 1 shows, schematically simplified, a blood treatment apparatus 1 according to the present invention, which is connected to a blood tubing set 3. The blood tubing set 3 features an arterial section 5 with an arterial needle 5a and an arterial patient tubing clamp 5c. The blood tubing set 3 further features a venous section 7 with a venous needle 7a and a venous patient tubing clamp 7c.

The blood tubing set 3 features a blood filter 9 with a membrane 11, for example a semi-permeable membrane. The membrane 11 divides the blood filter 9 into a blood chamber 13 and a dialysis fluid chamber 15.

The blood treatment apparatus 1 features a blood pump 17. The blood tubing set 3 features a venous drip chamber 19. The blood treatment apparatus 1 features a control or regulating apparatus 21 or is connected to this. The control or regulating apparatus 21 is connected to all the blood treatment apparatus's 1 components, or with the blood tubing set 3, or with both and influences them in the execution of the method according to the present invention.

Both the arterial needle 5a and the venous needle 7a are connected to the vascular system of a patient 35. The blood tubing set 3 features an optional arterial blood sensor 37', a venous blood sensor 39', or both.

The blood filter 9 is connected to a dialysis fluid supply line 37 and a dialysate discharge line 39, both of which are only shown here in sections. A possible flow direction within these two lines is shown with arrows.

A stub 41 leads out from the dialysate discharge line 39. This is in operative connection with an ultra-filtration pump 43.

Figure 2:
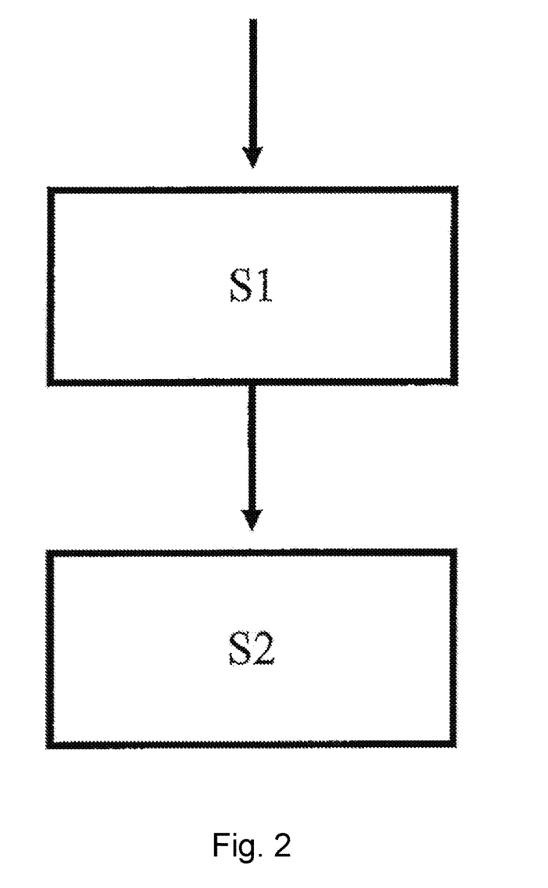
FIG. 2 schematically shows in a flow-diagram, the steps of the method according to the present invention in a first exemplary embodiment.

FIG. 2 shows, schematically simplified, as a flow-diagram, the steps of the method according to the present invention in a first exemplary embodiment.

In a first step s1, the venous patient tubing clamp 7c remains closed. The blood pump 17 pumps blood through the arterial needle 5a into the blood filter 9 with the arterial patient tubing clamp 5c open. There, a volume—in particular, a predetermined volume—enters the dialysis fluid chamber 15 from the blood chamber 13.

If the volume is predetermined, then, for example, the filling volume can correspond or correlate to the volume of the arterial section to the blood filter 9 (inclusive or exclusive of its volume or the volume of its blood chamber 15). This volume can optionally be measured in advance, (for example, using the pump running time). Hence, the blood flow rate can correspond to the ultra-filtration rate, and vice versa.

In a second step s2, the venous patient tubing clamp 7c is opened as soon as a sensor (not shown) detects blood in the blood filter 9 or in the region of the blood filter.

The method according to the present invention can be ended at this point by opening the patient tubing clamp 7c. Here, a treatment method which is no longer a part according to the present invention, can follow.

Figure 3:
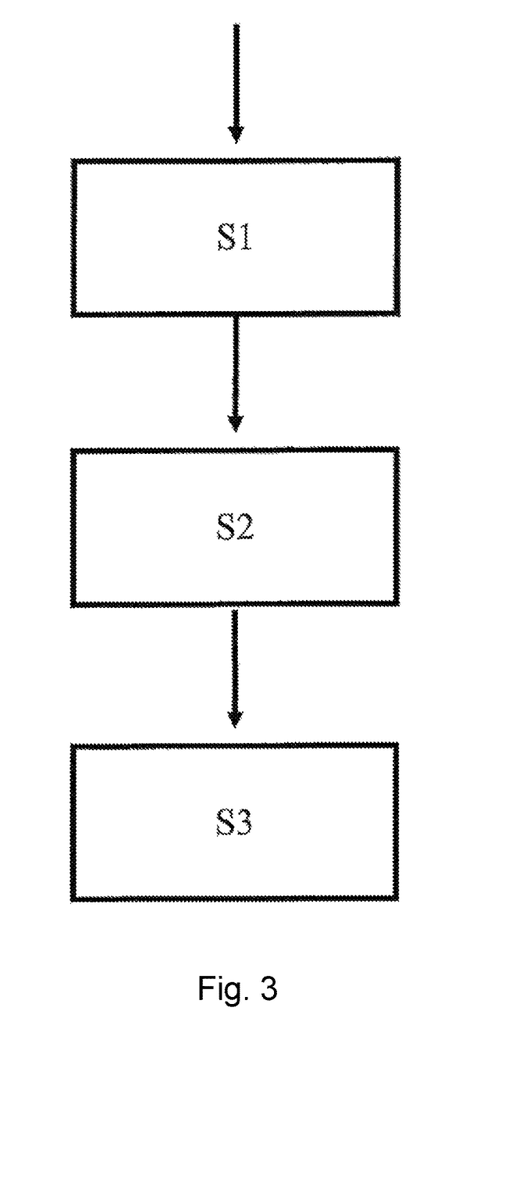
FIG. 3 shows schematically in a flow-diagram, the steps of the method according to the present invention in a second exemplary embodiment.

FIG. 3 shows, schematically simplified, as a flow diagram, the steps of the method according to the present invention in a second exemplary embodiment.

The steps s1 and s2 each correspond to those steps which are described with reference to FIG. 2.

In addition, there is a step s3, in which a control instruction to the blood treatment apparatus or a data carrier is issued. When the control instruction reaches the blood treatment apparatus, it causes filtration at a higher ultra-filtration rate in a first time period than in a second time period following. In this process, the first time period can lie after the end of the method according to the present invention. Hence, the first time period can lie at a time following the issue of the control instruction.

The control signal can cause the ultra-filtration rate to decrease within the first time period.

The control signal can cause a volume to be filtered across the membrane in the first time period which is higher than a volume which is filtered across the membrane in a second time period by the volume of the blood chamber of the blood tubing set and the section of the blood tubing set being downstream of the blood chamber.

At step s3, the treatment method can start which is no part of the present invention.

Figure 4:
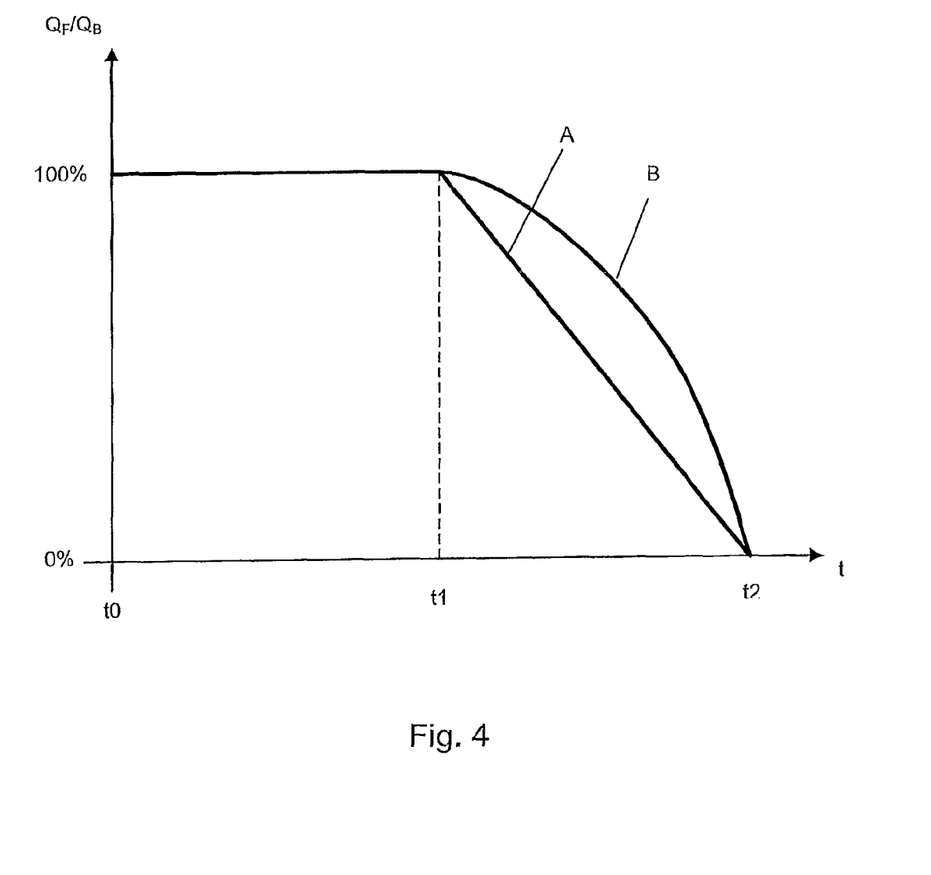
FIG. 4 shows, by way of example, the chronological progress of the ratio or proportion of fluid to blood volume flow in the blood chamber.

FIG. 4 shows, exemplarily, the chronological sequence of the ratio or proportion between fluid volume flow $Q_F$ (or ultra-filtrate volume flow $Q_{UF}$) and blood-volume flow $Q_B$ in the blood chamber.

In FIG. 4, the following applies:

$Q_F/Q_B$: ratio or proportion of fluid volume flow to blood volume flow.

100%: the volume flow in the blood chamber features only fluid and no blood

0%: the volume flow in the blood chamber features only blood and no fluid

Phase 1: time period between t0 and t1

Phase 2: time period between t1 and t2

A: linear time course of $Q_F/Q_B$ in phase 2, i.e., the fluid volume flow continually decreases in the blood chamber over time.

B: Non-linear time course of $Q_F/Q_B$ in phase 2; in the blood chamber the fluid volume flow decreases with less strength at first and then with increasing strength.

FIG. 5 shows possible time courses of the ultra-filtrate flows $Q_{UF}$ through the membrane between the blood chamber and the dialysis fluid chamber.

In FIG. 5 the following applies:

$Q_{UF}$: ultra-filtrate flow through the membrane between the blood chamber and the dialysis fluid chamber;

t3: Start of the treatment; t3 is that point at which a colour change and thereby the existence of blood is detected in the venous chamber by a sensor;

t4: End of the treatment;

C: non-linear decreasing progression, over the total treatment time, of the ultra-filtrate flow $Q_{UF}(t)$ which has been elevated by the remaining priming volume.

D: linear decreasing progression of the increased ultra-filtrate flow of $Q_{UF}(t)$ over the total treatment time; and E: ultra-filtrate flow $Q_{UF}(t)$, without taking into consideration the ultra-filtrate flow which has been elevated through the remaining priming volume; the course E can be a jump function, as shown in FIG. 5.

According to the present invention, the total ultra-filtrated volume, known as the treatment volume balance, can be determined using the following formula:

$$V_{UF,ges} = \int_{t3}^{t4} (Q_{UF}(t) + Q_{Priming}(t))dt,$$

$V_{UF,ges}$ total ultra-filtrated volume in the time interval t3 to t4 (treatment time);

$Q_{UF}(t)$: ultra-filtrate flow through the membrane between the blood chamber and the dialysis fluid chamber during the treatment time, without taking into consideration the additional ultra-filtrate flow; the integral corresponds to the area between the x axis and "E"; and $Q_{Priming}(t)$: additional ultra-filtrate flow on the basis of the remaining priming volume; the integral corresponds to the area between "E" and "C" or "D".

The time point t3 can concur with the time point t2 in FIG. 4, but does not have to. In any case, the time point t3 is after t2.

Figure 6:
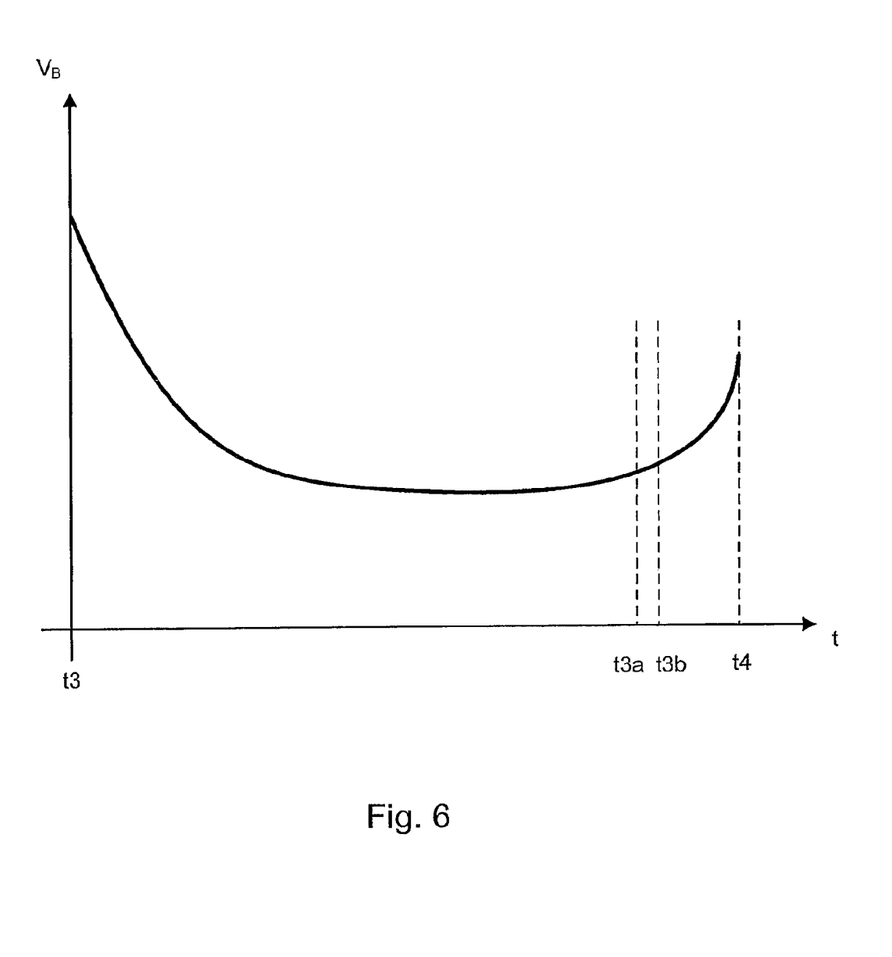
FIG. 6 shows one possible chronological sequence or time course for the patient's blood volume during the duration of the treatment.

FIG. 6 shows a possible time course for a patient's blood volume during the treatment duration.

The beginning of the treatment session is time point t3, the end is time point t4. During the whole treatment session volume is removed by the ultra-filtration from the blood.

At time point t3a a parameter as a measurement for the change in portion of plasma water in the patient's blood is determined. Then, at time point t3b or a time period following t3b or a time period encompassing t3b, an additional volume (e.g. a saline solution, supplied as an infusion) is given to the patient by infusion into the patient's blood volume. The volume supplied additionally can, for example, reduce or advantageously counteract an elevated volume compensation within the patient's two fluid compartments—the extra cellular matrix ECM and the blood vessels—after the end of the treatment session.

List of Reference Numerals

| Reference Numeral | Description |
| --- | --- |
| 1 | blood treatment apparatus |
| 3 | blood tubing set |
| 5 | arterial section |
| 5a | arterial needle |
| 5c | arterial patient tubing clamp |
| 7 | venous section |
| 7a | venous needle |
| 7c | venous patient tubing clamp |
| 9 | blood filter |
| 11 | membrane |
| 13 | blood chamber |
| 15 | dialysis fluid chamber |
| 17 | blood pump |
| 19 | venous drip chamber |
| 21 | control or regulating apparatus |
| 35 | patient |
| 37 | dialysis fluid supply line |
| 39 | dialysate discharge line |
| 41 | stub |
| 43 | ultra-filtration pump |

The invention claimed is:

1. A method for at least one of controlling or regulating a blood treatment apparatus having a blood pump for conveying blood inside an extra-corporeal blood tubing set, the extra-corporeal blood tubing set comprising or connected with (i) an arterial section having an arterial needle and an arterial patient tubing clamp, (ii) a venous section having a venous needle and a venous patient tubing clamp, and (iii) a blood filter arranged between the arterial section and the venous section, the blood filter having a membrane which separates a blood chamber from a dialysis fluid chamber, the method comprising:
conveying fluid into the extra-corporeal blood tubing set to prime the extra-corporeal blood tubing set;
while: (i) the extra-corporeal blood tubing set contains the fluid, (ii) the arterial and venous needles are connected to a patient's vascular system, (iii) the arterial patient tubing clamp is open, and (iv) the venous patient tubing clamp is closed, conveying with a pump, such as the blood pump or an ultra-filtration pump, a portion of the fluid through the membrane and into the dialysis fluid chamber;
after the conveying, performing a blood treatment of the patient by opening the venous patient tubing clamp and circulating, through the extra-corporeal blood tubing set and the patient's vascular system, the fluid remaining in the extra-corporeal blood tubing and blood of the patient; and
correcting a fluid balance of the patient by, during a first time period of the circulating, outputting a control instruction to the blood treatment apparatus to filter with an ultra-filtration rate that is higher or lower than during a second time period of the circulating following the first time period.

2. The method according to claim 1, wherein the portion of the fluid is conveyed until a predetermined fluid volume has passed into the dialysis fluid chamber or at least until a sensor signal transmits or detects that blood has reached a predetermined location.

3. The method according to claim 2, further comprising: reducing or stopping the conveying of the portion of the fluid after the predetermined fluid volume has passed into the dialysis fluid chamber or at least when the sensor signal transmits that blood has reached the predetermined location.

4. The method according to claim 2, wherein the fluid is a priming solution, wherein the priming solution is conveyed via the blood pump out of the arterial section through the membrane and into the dialysis fluid chamber.

5. The method according to claims 1, wherein the predetermined fluid volume corresponds to a total volumetric capacity of the extra-corporeal blood tubing set.

6. The method according to claim 1, wherein the ultra-filtration rate is higher during the first time period than during the second time period.

7. The method according to claim 1, wherein the ultra-filtration rate is lower during the first time period than during the second time period.

8. The method according to claim 6, wherein the control instruction causes the ultra-filtration rate to decrease in the first time period.

9. The method according to claim 7, wherein the control instruction causes the ultra-filtration rate to decrease in the first time period.

10. The method according to claim 6, wherein, during the first time period, a volume is filtered through the membrane which is higher than a volume which is filtered through the membrane during the second time period by a volume capacity of the blood chamber and the venous section.

11. The method according to claim 7, wherein, during the first time period, a volume is filtered through the membrane which is higher than a volume which is filtered through the membrane during the second time period by a volume capacity of the blood chamber and the venous section.

12. The method according to claim 8, wherein, during the first time period, a volume is filtered through the membrane which is higher than a volume which is filtered through the membrane during the second time period by a volume capacity of the blood chamber and the venous section.

13. The method according to claim 9, wherein, during the first time period, a volume is filtered through the membrane which is higher than a volume which is filtered through the membrane during the second time period by a volume capacity of the blood chamber and the venous section.

14. The method according to claim 1, further comprising:
determining a plasma water portion in the blood at a first point of time at a start of the blood treatment and at a second point of time at an end of the blood treatment;
outputting a control instruction to the blood treatment apparatus to filter with a first ultra-filtration rate between the first point of time and the second point of time;
optionally determining a volume filtered at the first ultra-filtration rate based at least on a determining of the plasma water portion at a time point between the first point of time and the second point of time; and
administering an additional fluid into the extra-corporeal blood tubing set or into the patient's vascular system at a further time point between the first point of time and the second point of time.

15. The method according to claim 14, wherein the additional fluid is administered such that, at the second point of time, the plasma water portion or a fraction of the blood assumes a predetermined value or lies within a predetermined range of values.

16. The method according to claim 14, further comprising:
determining a blood volume of the patient at the second point of time.

17. A control or regulating apparatus cooperating with the blood treatment apparatus and arranged or configured to carry out the method according to claim 1.

18. A blood treatment apparatus comprising:
the control or regulating apparatus according to claim 17.

19. The blood treatment apparatus according to claim 18, wherein the blood treatment apparatus is arranged for dialysis, acute dialysis, chronic dialysis or aquapheresis.

* * * * *

UNITED STATES PATENT AND TRADEMARK OFFICE
CERTIFICATE OF CORRECTION

PATENT NO. : 10,449,285 B2
APPLICATION NO. : 14/905431
DATED : October 22, 2019
INVENTOR(S) : Paul Chamney, Pascal Kopperschmidt and Wolfgang Wehmeyer It is certified that error appears in the above-identified patent and that said Letters Patent is hereby corrected as shown below:

In the Claims

Column 16, Line 35, Claim 5, delete "claims 1," and insert --claim 2--.

Signed and Sealed this
Twenty-first Day of January, 2020

Andrei Iancu
*Director of the United States Patent and Trademark Office*